(12) United States Patent
Kunz et al.

(10) Patent No.: US 9,579,526 B2
(45) Date of Patent: Feb. 28, 2017

(54) RADIATION THERAPY DEVICE WITH FREELY CUSTOMIZABLE SOURCE AND IMAGER MOTION TRAJECTORY

(75) Inventors: Patrik Kunz, Baden (CH); Timo Berkus, Ennetbaden (CH); Markus Oelhafen, Rohr (CH); Reto Filiberti, Steinhausen (CH)

(73) Assignee: Varian Medical Systems International AG, Cham (CH)

( * ) Notice: Subject to any disclaimer, the term of this patent is extended or adjusted under 35 U.S.C. 154(b) by 0 days.

(21) Appl. No.: 12/364,222

(22) Filed: Feb. 2, 2009

(65) Prior Publication Data

US 2010/0195792 A1    Aug. 5, 2010

(51) Int. Cl.
| | | |
|---|---|---|
| A61B 6/03 | (2006.01) | |
| A61N 5/10 | (2006.01) | |
| A61B 6/00 | (2006.01) | |
| A61B 6/02 | (2006.01) | |

(52) U.S. Cl.
CPC ............ *A61N 5/1049* (2013.01); *A61B 6/027* (2013.01); *A61B 6/032* (2013.01); *A61B 6/4429* (2013.01); *A61B 6/4452* (2013.01); *A61B 6/4458* (2013.01); *A61B 6/4441* (2013.01); *A61B 6/482* (2013.01); *A61N 2005/1061* (2013.01)

(58) Field of Classification Search
CPC .. A61B 6/03; A61B 6/032; A61B 6/46; A61B 6/467; A61B 6/54; A61N 5/1061; A61N 5/1074
See application file for complete search history.

(56) References Cited

U.S. PATENT DOCUMENTS

| | | | |
|---|---|---|---|
| 6,435,715 B1 | 8/2002 | Betz et al. | |
| 6,888,919 B2 * | 5/2005 | Graf | 378/65 |
| 7,130,372 B2 * | 10/2006 | Kusch et al. | 378/65 |
| 7,444,011 B2 * | 10/2008 | Pan et al. | 382/131 |
| 7,657,304 B2 * | 2/2010 | Mansfield et al. | 600/427 |
| 2003/0091156 A1 | 5/2003 | Crain et al. | |
| 2004/0068169 A1 * | 4/2004 | Mansfield et al. | 600/407 |

FOREIGN PATENT DOCUMENTS

| | | |
|---|---|---|
| EP | 0220501 A1 | 5/1987 |
| WO | 2006042211 A2 | 4/2006 |

* cited by examiner

*Primary Examiner* — Thomas R Artman

(57) ABSTRACT

Embodiments of the claimed subject matter provide a radiation therapy system for the acquisition of volumetric imaging with advanced trajectories. Embodiments include a device for applying diagnostic and therapeutic radiation to a target volume disposed in a patient subject, wherein volumetric imaging is acquired with advanced trajectories without displacing the patient subject. In one embodiment, a radiation therapy device is provided comprising: a gantry with a radiation source and a plurality of independent robotic arms mounted to the gantry, wherein an X-ray source is attached to an end of one robotic arm; and an imager attached to an end of another second robotic arm.

22 Claims, 9 Drawing Sheets

RADIATION THERAPY DEVICE WITH FREELY CUSTOMIZABLE SOURCE AND IMAGER MOTION TRAJECTORY

TECHNICAL FIELD

The present invention pertains generally to radiation therapy and, in particular, involves a radiotherapy machine used in radiation treatment applications.

BACKGROUND

Radiation therapy for the treatment of cancer is well known. Typically, radiation therapy involves focusing a beam of X-ray radiation into a target volume to diagnose an afflicted area or monitor a tumor or lesion. A beam of high energy x-ray radiation or electron radiation ("therapeutic radiation") is subsequently directed into the monitored area to treat the area. The area is further monitored to ensure an appropriate positioning of the therapeutic radiation beam. Radiation therapy devices are commonly equipped with linear accelerators used to generate either (or both) electron radiation or X-ray radiation.

A typical configuration for a radiation therapy device includes a radiation source for emitting the therapeutic x-ray radiation, an X-ray source for emitting the X-ray radiation for imaging and one or more imaging devices corresponding to a radiation source for receiving incoming radiation after passing through the target volume. The beams collected by the imagers are used to generate a display (i.e., one or more images) of the targeted volume.

Newer technology and advanced techniques allow for improved image collection. A recent development in the field of computerized tomography is the use of a cone-beam computerized tomography system. A cone beam computerized tomography system is similar to that of a conventional computerized tomography system, with the exception that an entire volumetric image is acquired through rotation of the source and imager. This is made possible by the use of a two-dimensional (2D) imager. A plurality of two dimensional images at various angles is collected. From these two dimensional images, the cone beam computerized tomography system reconstructs three-dimensional images according to various methods and algorithms.

In conventional computerized tomography systems, one or more 2D slices are reconstructed from one dimensional projections of the patient, and these slices may be combined to form a three dimensional (3D) image of the patient. In contrast, in cone beam computerized tomography, a fully 3D image is reconstructed from a plurality of 2D projections. Cone beam computerized tomography offers a number of advantages, including: formation of a 3D image of the patient from a single rotation about the patient (whereas conventional computerized tomography typically requires a rotation for each slice); spatial resolution that is largely isotropic (whereas in conventional computerized tomography the spatial resolution in the longitudinal direction is typically limited by slice thickness); and considerable flexibility in the imaging geometry.

Radiation therapy subjects typically receive treatment in a supine position. Traditional configurations consist of an overhead radiation source directing radiation into a targeted volume within a prone subject positioned directly below the radiation source. Unfortunately, diagnostic imaging performed during the application of radiation therapy to a target volume from a single angle and direction may often be ineffective. For example, diagnostic imaging from conventional computerized tomography systems may be obscured by other content (e.g., anatomy) within the target volume.

In recently developed radiation therapy devices, the structures supporting the radiation source have become configured to be capable of rotation along one axis (typically, around the target subject). Even more recently, radiation therapy devices with a plurality of supporting structures each attached to a radiation source or imager configured to rotate around the same axis have been developed. FIG. 1 depicts a conventional radiation therapy device with two rotatable gantries, each supporting a radiation source. FIG. 1 includes a first gantry attached to a therapeutic radiation source, a second gantry attached to a diagnostic radiation source, a multiple-energy imaging unit for receiving radiation passing from both radiation sources, and a couch upon which the patient subject is positioned. The gantries and affixed radiation sources rotate around the subject to generate a volumetric image.

However, the solution of rotating one or more support structures around a single axis for diagnostic purposes restricts the volumetric imaging acquisition process to very limited trajectory shapes. For example, a support structure which rotates around a shared axis is capable of only circular, spiral and spherical trajectories. Unfortunately, volumetric imaging along a single axis of rotation may be incomplete. Furthermore, rotatable gantries typically rotate along a fixed circumference and may not be adjustable. Accordingly, this prevents images from being acquired at a greater proximity ("zooming") which would allow for a greater resolution of a smaller target volume.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Embodiments of the present invention are directed to a flat panel imager cone beam computer tomography system mounted on a radiation therapy machine allowing for volumetric computer tomography acquisition with freely customizable arbitrary source and imager motion trajectory during image acquisition.

In one embodiment, the flat panel imager cone beam computer tomography consists of two independent robotic arms, one for the X-ray tube (source arm) and one for the flat panel X-ray imager. These robotic arms allow for positioning of the X-ray source and the flat panel imager to any position in space within the travel range of the robotic arm. This capability is combined with a flexible motion control system for the robotic arms and with the rotation capability of the main gantry of the radiation therapy device. This combination allows the acquisition of volumetric computer tomography images with any customizable motion trajectory. The advantages of customizable motion trajectories are manifold, compared to the standard circular trajectories usually applied on cone beam computer tomography systems mounted on radiation therapy machines.

The most obvious advantage of increasing (e.g., doubling) the axial coverage of a single cone beam computer tomography scan can be achieved by combining two half circular acquisitions with an intermediate line segment. Other more sophisticated motion trajectories (circle and line, saddle) combined with dedicated reconstruction algorithms will reduce the cone beam artifacts caused by the incompleteness of a circular trajectory projection set, thereby increasing the overall 3D image quality of the cone beam artifact in the 3D images and therefore increasing the overall 3D image quality.

The system will not only allow for flexible, variable and customizable acquisition trajectories but also for freely selectable source/imager distance. This allows zoomed acquisition (e.g., for smaller objects) to increase the resulting image resolution and providing superior image quality compared to other cone beam computer tomography systems mounted to a radiation treatment system.

Embodiments of the invention would also allow for non-orthogonal projection. This would allow tomosynthesis like 3D image acquisition without the need of either gantry or patient/table motion.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
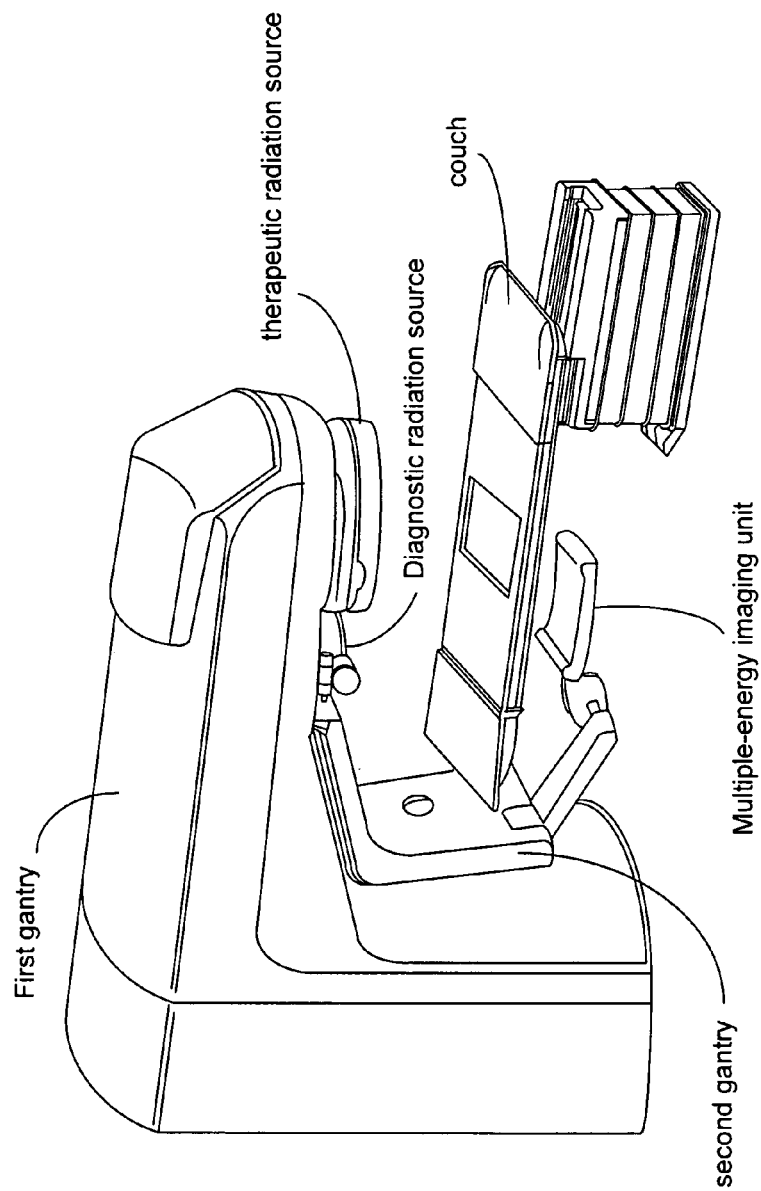
FIG. 1 is an illustration of a radiotherapy machine having two rotatable gantries and a multiple-energy imaging unit.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in a figure herein (e.g., FIGS. 8, 9) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

In the following embodiments, a radiation therapy system is described for the acquisition of volumetric imaging. Embodiments include a device for applying diagnostic and therapeutic radiation to a target volume disposed in a patient subject, wherein volumetric imaging is acquired in advanced trajectories without displacing the patient subject.

Exemplary Radiation Therapy Device

Figure 2:
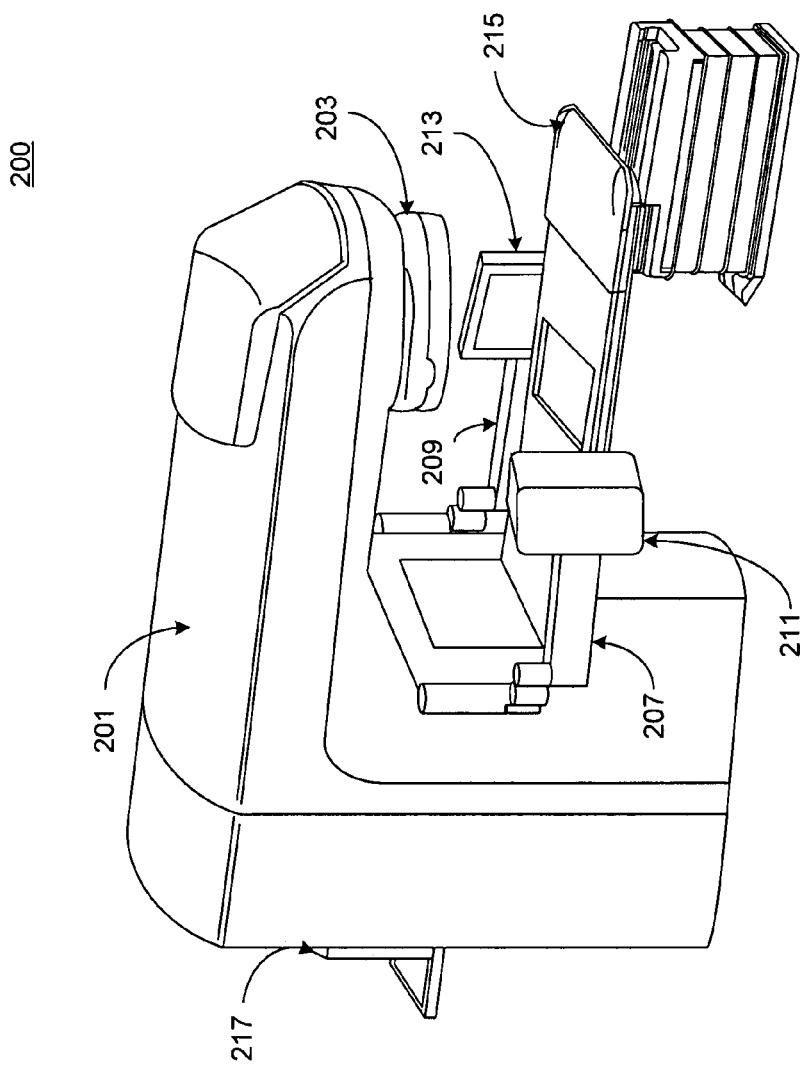
FIG. 2 is an illustration of a radiotherapy device, in accordance with one embodiment.

With reference now to FIG. 2, an illustration of an example of a radiation therapy device 200 is depicted, in accordance with one embodiment. In one configuration, radiation therapy device 200 includes a support structure (e.g., gantry 201), a therapeutic radiation source 203, a plurality of robotic arms (e.g., robotic arms 207, 209), a diagnostic radiation source 211, a diagnostic radiation imager 213, and a patient couch 215. In some embodiments, radiation therapy device 200 may include a communicatively coupled computing device 217.

In one embodiment, the end of gantry 201 positioned above patient couch 215 is attached to a therapeutic radiation source 203. A plurality of robotic arms 207 and 209 is further mounted on the gantry 201. In some embodiments, the plurality of robotic arms 207 and 209 may be extendable and retractable. In further embodiments, the plurality of robotic arms 207 and 209 are independent from each other and opposable. In one embodiment, a diagnostic radiation source 211 is coupled to the end of a robotic arm (e.g., robotic arm 207) extending towards patient couch 215. In further embodiments, a diagnostic radiation imager 213 is coupled to the end of an alternate robotic arm (e.g., robotic arm 209), also extending towards patient couch 215. The robotic arms 207 and 209 are capable of maneuvering to allow for positioning of the diagnostic radiation source 211 and the diagnostic radiation imager 213 to any position in space within the travel range of the robotic arm. In still further embodiments, the gantry 201 is also rotatable along one or more axes, allowing for even greater travel ranges for the plurality of robotic arms 207 and 209.

While receiving treatment, a patient is positioned (typically supine) on patient couch 215. A target volume (generally disposed within or about the patient subject) is acquired. According to one embodiment, the target volume is acquired by generating a volumetric image of the area within the patient. A volumetric image of the area is acquired by, for example, generating a three dimensional image using diagnostic radiation source 211 in conjunction with diagnostic radiation imager 213. In one embodiment, diagnostic radiation source 211 may comprise, for example, an X-ray radiation source. The robotic arm 207 attached to diagnostic radiation source 211 can be positioned about the target volume for computer tomography images using a cone X-ray beam to acquire volumetric information. Positioning of the robotic arm 207 may be performed by movement of the robotic arm 207 which may include, but is not limited to, rotating, swiveling, extending and retracting the robotic arm.

In one embodiment, diagnostic radiation source 211 and diagnostic radiation imager 213 may be positioned around a target volume such that the target volume is between the diagnostic radiation source 211 and diagnostic radiation imager 213 while volumetric imaging is being acquired. The radiation (e.g., X-rays) emitted by the diagnostic radiation source 211 travel through the target subject, are received by the diagnostic radiation imager 213 and an image of the target subject is thus generated, in accordance with conventional techniques. The imaging generated from the diagnostic radiation process is subsequently utilized to provide targeting information which can be used to accurately direct the therapeutic radiation from therapeutic radiation source 203 to the target volume from various angles.

In one embodiment, the diagnostic radiation imager 213 can be attached to a second robotic arm 209 opposite from the robotic arm 207 attached to diagnostic radiation source 211. In further embodiments, the robotic arm 209, though still independent of, attached to the diagnostic radiation imager 213 is positioned in concert with the robotic arm 207, such that the diagnostic radiation imager 213 is in constant alignment to diagnostic radiation source 211 and on a side opposite diagnostic radiation source 211 with respect to the target volume.

Once aligned, diagnostic radiation (e.g., diagnostic X-rays) from the diagnostic radiation source 211 is propagated towards the target volume situated on or about the patient couch 215. The diagnostic radiation passes through the target volume and is received by the diagnostic radiation imager 213. The resulting image(s) generated by the diagnostic radiation imager 213 may then be used to re-position the patient using the patient couch 215 to achieve a greater degree of accurate targeting. The therapeutic radiation source 203 subsequently propagates the therapeutic radiation into the target volume within the re-positioned patient.

The robotic arm 207 can extend or retract the attached diagnostic radiation source 211 to position the diagnostic radiation source 211 such that images are obtained with a smaller viewing field but with greater resolution (e.g., zoomed). Alternatively, the robotic arm 207 may be positioned to provide clearance around the geometry (e.g., to avoid obscuring a direct beam or line) of the therapeutic radiation source 203 attached to the gantry 201. The diagnostic radiation source 211 can be extended and retracted, via extension/retraction respectively, of robotic arm 207. In further configurations, the robotic arm 207 may be positioned to place the diagnostic radiation source 211 in a plurality of positions about the target volume (e.g., via rotation around one or more axes). In one embodiment, each of the robotic arms 207 and 209 is capable of pivoting at a plurality of pivot points and along a plurality of independent axes.

In further embodiments, each of the plurality of robotic arms 207 and 209 may be equipped with mechanisms (e.g., mechanical or pneumatic components) that allow the robotic arm to be raised or lowered, and other movements typical of independent articulation as known to one skilled in the art. In still further embodiments, each of the plurality of robotic arms 207 and 209 may be capable of retracting the position of the attached device (e.g., diagnostic radiation source 211 and diagnostic radiation imager 213) into a position convenient for storage (e.g., fully retracted, underneath the patient couch 215) during periods of non-use.

In some embodiments, positioning of the diagnostic radiation source 211 and diagnostic radiation imager 213 via the attached corresponding robotic arms (e.g., robotic arm 207 and 209) is performed automatically. The maneuvering of each of the robotic arms 207 and 209 may be executed, for example, according to a pre-programmed trajectory and executed by a flexible motion control system. The trajectory may be generated (programmed) via a flexible motion control system instantiated in a communicatively coupled computing device 217 having a processor and a memory and operable to receive and/or generate trajectories. According to one embodiment, a trajectory for a specific target volume and patient subject may be generated so that an imaging of the target volume may be acquired from a variety of angles customized to the patient subject and/or the target volume.

For example, a trajectory customized for the patient or target volume may be input into (or generated by) an interface instantiated in the communicatively coupled computing device 217. Computing device 217 may be mounted on the gantry 201, or may be coupled to the radiation therapy device 200 via one or more data transport cables. In further embodiments, computing device 217 may communicate with the radiation therapy device 200 remotely. Once initiated, the imaging acquisition process may position the robotic arms 207 and 209 coupled to the diagnostic radiation source 211 and diagnostic radiation imager 213 to acquire a volumetric image along the customized trajectory. In further embodiments, trajectories more flexible than conventional circular trajectories such as saddle-shaped trajectories and circle and line trajectories may be acquired and constructed.

As discussed above, a volumetric image may be constructed from a plurality of images acquired by positioning diagnostic radiation source 211 and diagnostic radiation imager 213. Once a volumetric image has been constructed for a target volume, the target volume may be re-positioned (e.g., by re-positioning the patient) to receive therapeutic radiation from the therapeutic radiation source 203 such that the therapeutic radiation may be directed into the target volume with greater precision with respect to the original (or former) position of the target volume (patient).

Figure 3:
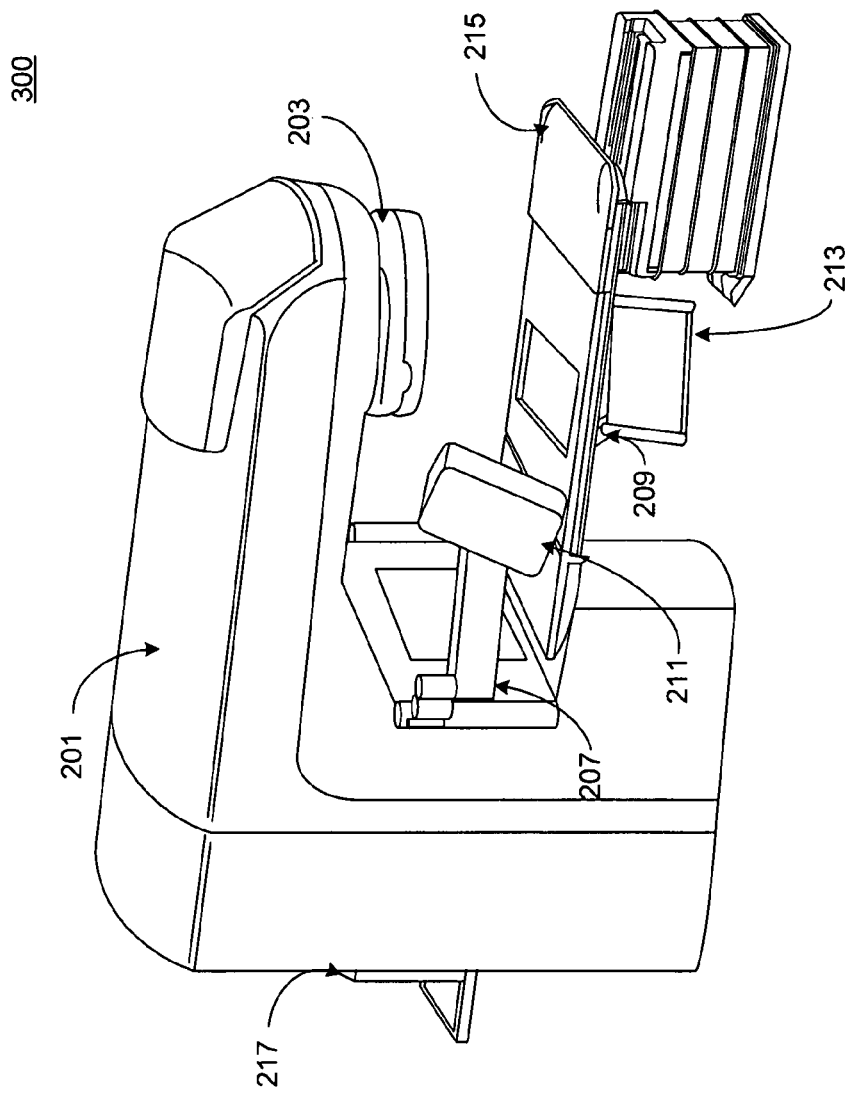
FIG. 3 is an illustration of an alternate configuration of a radiotherapy device, in accordance with one embodiment.

FIG. 3 is an illustration of an alternate configuration of a diagnostic radiation therapy device 300, such as a computer tomography system, in accordance with various embodiments. In one configuration, computer tomography system 300 includes the gantry 201, a plurality of robotic arms (e.g., robotic arms 207, 209), diagnostic radiation source 211, patient couch 215 and computing device 217 as described in detail with respect to FIG. 2. As depicted, FIG. 3 illustrates an exemplary configuration of a diagnostic radiation source 211 and an exemplary complementary position of a corresponding diagnostic radiation imager 213. In one configuration, the computer tomography system 300 may be used for the acquisition of three-dimensional volumetric images, and not to administer therapeutic radiation. In alternate embodiments, the computer tomography system 300 may be configured to include a therapeutic radiation source 203. As depicted, device 300 includes the diagnostic radiation source 211 and the diagnostic radiation imager 213 of FIG. 2.

In one embodiment, diagnostic radiation imager 213 may be configured to receive radiation from the diagnostic radiation source 211 in a plurality of positions. For example, the diagnostic radiation imager 213 may be positioned to align with (and be opposite to) the diagnostic radiation source 211 to receive radiation from diagnostic radiation source 211.

Positioning of the diagnostic radiation imager 213 may be performed by manually-induced movement of the attached robotic arm 209, as detailed above. Likewise, positioning of the diagnostic radiation imager 213 may be performed automatically. Similarly, the automatic positioning of the robotic arm 209 may be executed, for example, according to a pre-programmed trajectory programmed via a communicatively coupled computing device 217 operable to receive and/or generate trajectories. Accordingly, a trajectory customized for a specific target volume and patient subject may be generated by the diagnostic radiation imager 213 so that an imaging of the target volume may be acquired from a variety of angles.

As detailed above, robotic arm 209 may be capable of retracting the position of the attached diagnostic radiation imager 213 into a position convenient for storage (e.g., fully retracted, underneath the patient couch 215) during periods of non-use.

Exemplary Advanced Trajectories

Figure 4:
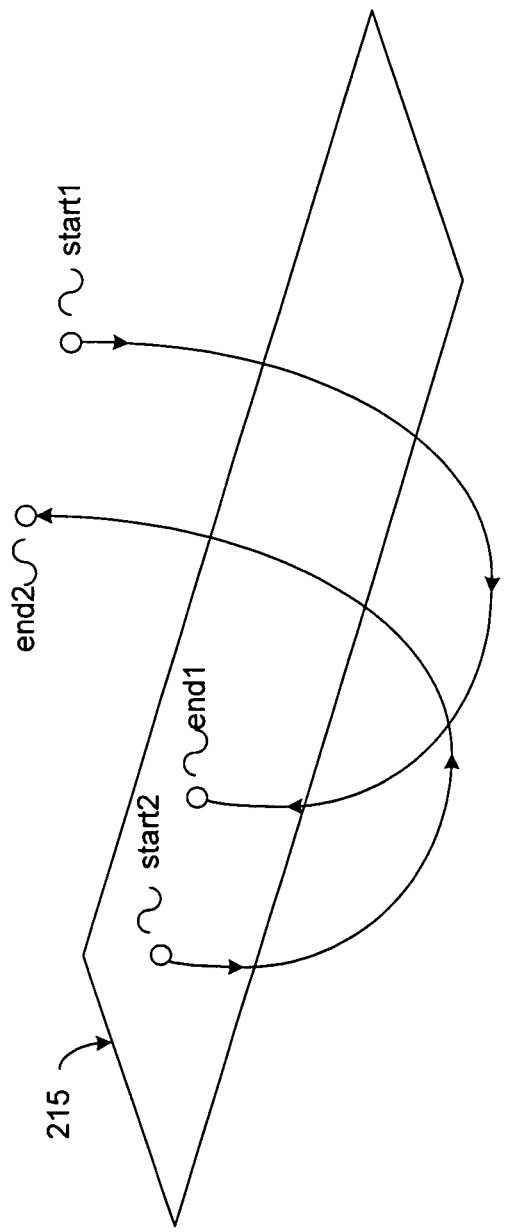
FIG. 4 is an illustration of an exemplary advanced trajectory of the diagnostic source for acquiring an advanced dual cone beam computer tomography scan in accordance with one embodiment.

FIG. 4 depicts an advanced trajectory of the diagnostic source 211 around a patient couch 215 for acquiring an advanced dual cone beam computer tomography scan. Although not shown in FIG. 4, the diagnostic radiation imager 213 can be similarly moved along a trajectory such that it is aligned with the source 211 as previously described herein. The image acquired is a composite of two half scan acquisitions (one clockwise and the other counter-clockwise) with an intermediate linear motion of the diagnostic radiation source and imager.

A possible starting position (start) for an example of a dual cone beam computer tomography scan is provided. Data will be acquired during the trajectory in the direction as indicated. A possible starting position (start) and ending position (end) for the positions of the diagnostic radiation source 211 are provided. According to the example of the trajectory according to FIG. 4, the movements of the independent robotic arms (e.g., robotic arm 207 and 209) in combination with rotation of the gantry 201 with respect to the patient couch 215 moves the diagnostic radiation source 211 from the starting position to the end position along the indicated trajectory, and the diagnostic imager 213 along a corresponding trajectory.

This approach allows a reconstruction of a doubled axial scan range by allowing the automatic combining of the volumes of the two half-scans. In one embodiment, the trajectory may be traveled as a plurality of non-contiguous shorter trajectories. This advanced acquisition trajectory is accomplished by moving the plurality of robotic arms without a need for displacing the patient, whereas with conventional computer tomography equipment, this trajectory may not be possible.

Figure 5:
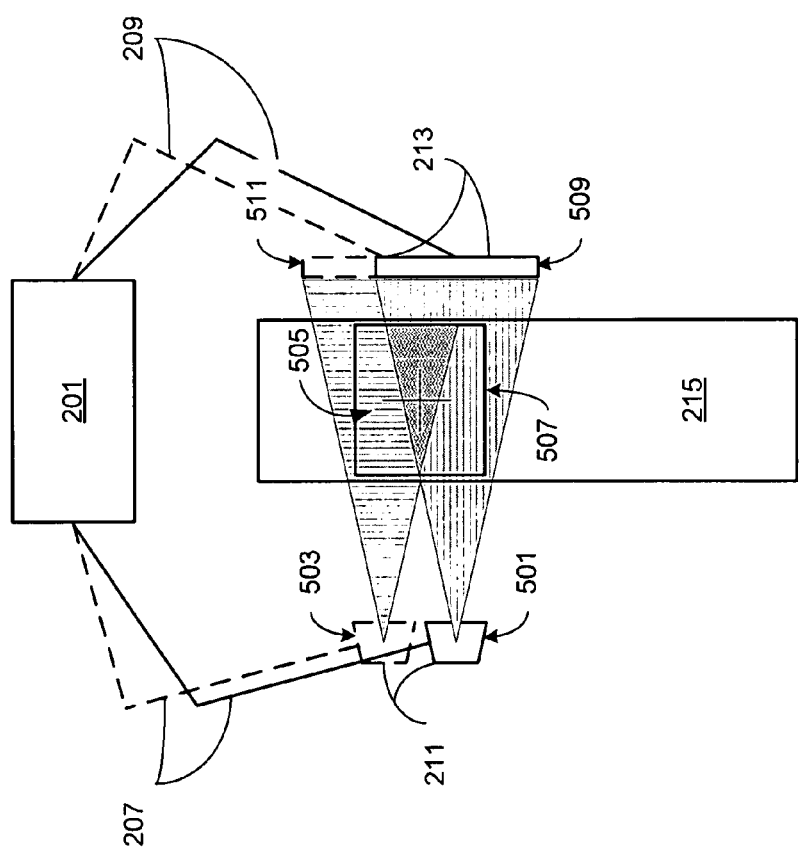
FIG. 5 is an illustration of a schematic diagram depicting exemplary positions of the robotic arms of a radiation therapy device to allow for a motion trajectory, in accordance with one embodiment.

FIG. 5 is an illustration of a schematic diagram depicting exemplary positions of the robotic arms of a radiation therapy device to allow for a motion trajectory according to one embodiment. At each of the positions, a scan will be acquired. As presented, FIG. 5 depicts a radiation device having a supporting structure (e.g., gantry 201) with a plurality of robotic arms (e.g., robotic arm 207 and 209) mounted on the supporting structure and extending towards a patient subject positioned on patient couch 215. A diagnostic radiation source 211 is attached to one end of a robotic arm 207. A diagnostic radiation imager 213 is attached to one end of an alternate robotic arm 209.

Each of the robotic arms 207 and 209 acquire imaging data along a plurality of positions comprising a trajectory. The trajectory may, for example, comprise a pre-programmed and/or customized trajectory for the particular patient subject. A plurality of positions 501 and 503 indicate an exemplary displacement of diagnostic radiation source 211 comprising a motion in the trajectory. Likewise, a plurality of positions 509 and 511 indicate exemplary displacement of diagnostic radiation imager 213 corresponding to the displacement of diagnostic radiation source 211. The crosshairs 507 indicate the treatment isocenter. The target box 505 depicts the total scan volume available for reconstruction.

Figure 6:
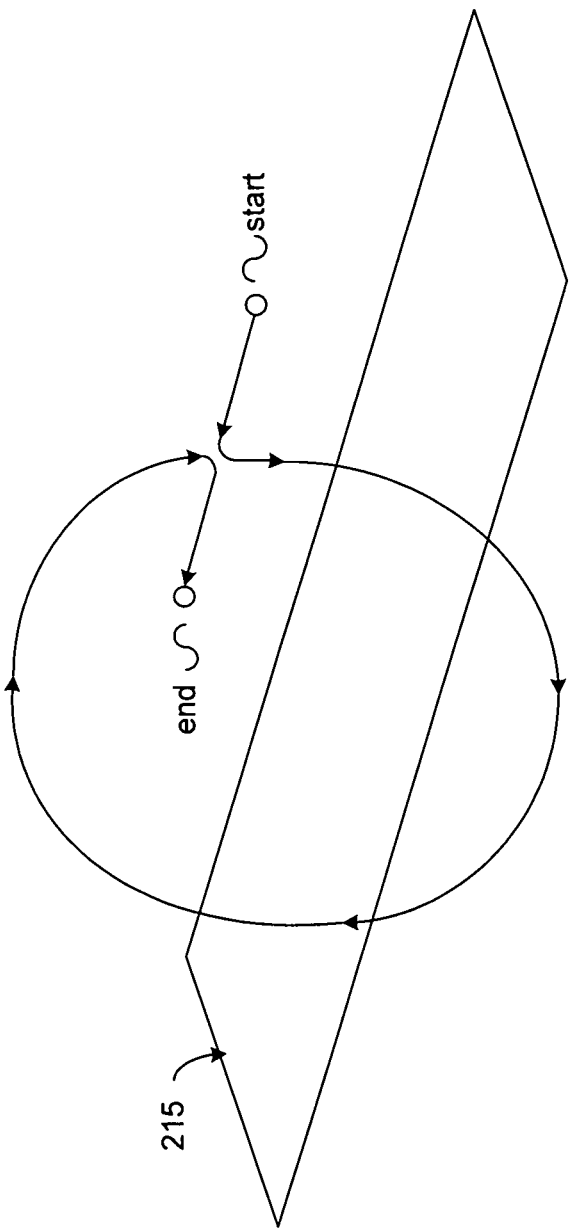
FIG. 6 depicts an advanced trajectory of the diagnostic radiation source for acquiring a circle and line trajectory cone beam computer tomography scan, in accordance with one embodiment.

FIG. 6 depicts an advanced trajectory of the diagnostic radiation source 211 around a patient couch 215 for acquiring a circle and line trajectory cone beam computer tomography scan. The acquisition is a composite of two linear motions and an intermediate full 360 degree rotation. A possible starting position (start) and ending position (end) for the diagnostic radiation source 211 are provided. Data is acquired while traveling in the direction as indicated. According to the example of the trajectory according to FIG. 6, the movements of the independent robotic arms (e.g., robotic arm 207 and 209) in combination with rotation of the gantry 201 with respect to the patient couch 215 moves the diagnostic radiation source 211 from the starting position to the end position along the indicated trajectory, and the diagnostic imager 213 along a corresponding trajectory.

This approach allows a reconstruction of the full volume with the advantage of reducing the so-called cone beam image artifact (which occurs in conventional circular cone beam computer tomography acquisition trajectories). In one embodiment, the trajectory may be traveled as a plurality of non-contiguous shorter trajectories. This advanced acquisition trajectory is accomplished by moving the plurality of robotic arms without a need for displacing the patient, whereas with conventional computer tomography equipment, this trajectory may not be possible.

Figure 7:
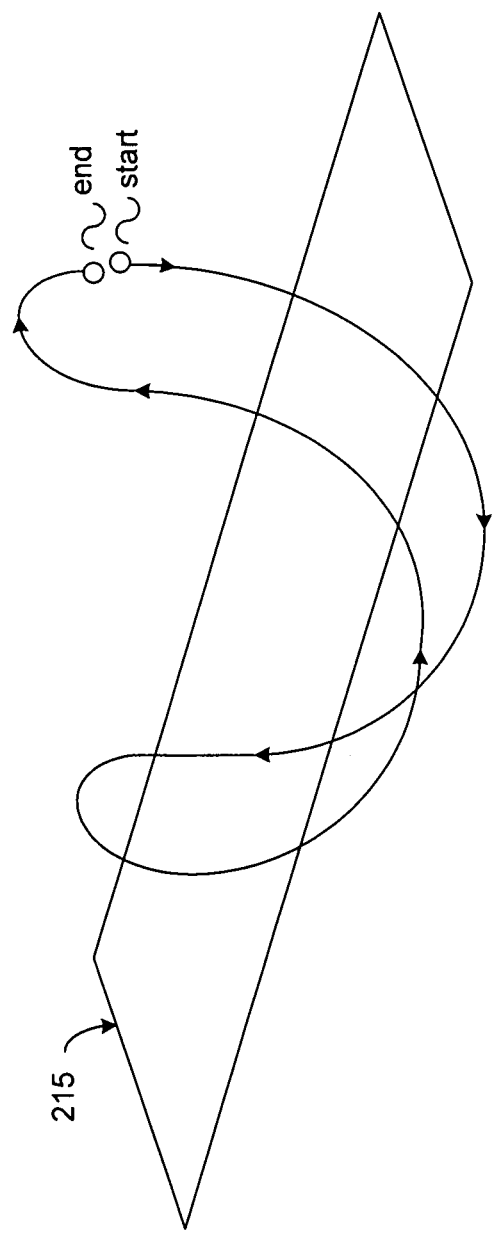
FIG. 7 depicts an advanced trajectory of the diagnostic radiation source for acquiring a saddle cone beam computer tomography scan, in accordance with one embodiment.

FIG. 7 depicts an advanced trajectory of the diagnostic radiation source 211 around a patient couch 215 for acquiring a saddle cone beam computer tomography scan. A possible starting position (start) and ending position (end) for the positions of the diagnostic radiation source 211 are provided. Data is acquired along the trajectory as indicated.

According to the example of the trajectory according to FIG. 7, the movements of the independent robotic arms (e.g., robotic arm 207 and 209) in combination with rotation of the gantry 201 with respect to the patient couch 215 moves the diagnostic radiation source 211 from the starting position to the end position along the indicated trajectory, and the diagnostic imager 213 along a corresponding trajectory.

This approach allows a reconstruction with increased volume (via increased axial coverage) while reducing the cone beam image artifact. In one embodiment, the trajectory may be traveled as a plurality of non-contiguous shorter trajectories. This allows for image acquisition according to advanced acquisition trajectories by moving the robotic arms without displacing the patient, whereas with conventional computer tomography equipment, this trajectory may not be feasible.

Applying Radiation

Figure 8:
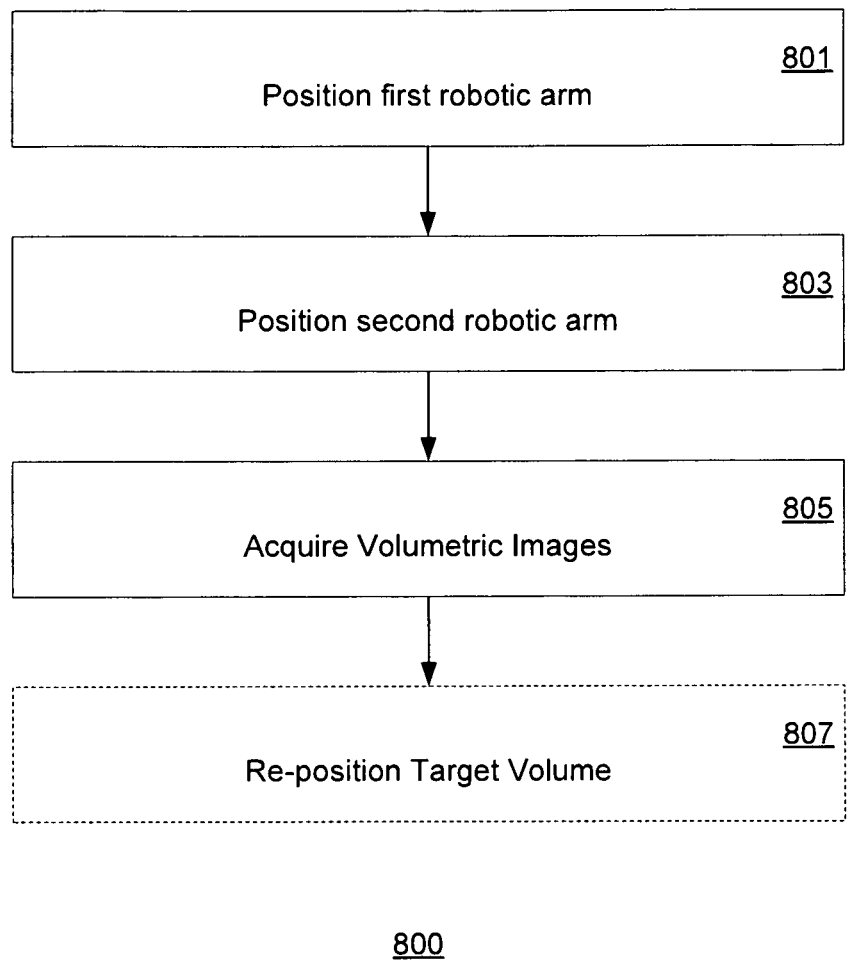
FIG. 8 is a flowchart of one embodiment of the method for positioning a radiation therapy device to apply radiation in accordance with one embodiment.

FIG. 8 is a flowchart 800 of one embodiment of the method for positioning a radiation therapy device to apply radiation in accordance with one embodiment. Steps 801-807 describe exemplary steps comprising the process depicted in flowchart 800 in accordance with the various embodiments herein described. In one embodiment, the flowchart 800 is implemented as computer-executable instructions stored in a computer-readable medium.

At step 801, a first robotic arm 207 coupled to a diagnostic radiation source 211 is positioned along a trajectory to be in alignment with a target volume. In one embodiment, the diagnostic radiation source 211 is a diagnostic X-ray source. The target volume may be disposed in or about a subject positioned on patient couch 215. In one embodiment, the subject is positioned in a supine position and supported by patient couch 215. In further embodiments, the diagnostic radiation source 211 is positioned along a pre-programmed trajectory customized for the patient.

At step 803, a second robotic arm 209 coupled to an imager 213 is positioned along a trajectory to receive radiation from the diagnostic radiation source 211 after the radiation has traveled through the target volume. According to some embodiments, steps 801 and 803 are performed simultaneously.

At step 805, data from the radiation received in the imager 213 may be used to generate an image of the target volume. In one embodiment, the data from the radiation received in the imager 213 is used to generate a plurality of three-dimensional volumetric images of the target volume. The three-dimensional volumetric images of the target volume may be displayed, for example, in computing device 217. In further embodiments, the imager 213 is positioned along a pre-programmed trajectory corresponding to a pre-programmed trajectory of diagnostic radiation source 211 and is customized for the patient. In yet further embodiments, the trajectories traveled by the diagnostic radiation source 211 and imager 213 and attached robotic arms 207 and 209 are programmed into, and generated by, for example, a motion control system executing on computing device 217.

At optional step 807, data acquired by the imager 213 in step 805 may be used to reposition the patient to be in alignment with the target volume.

Figure 9:
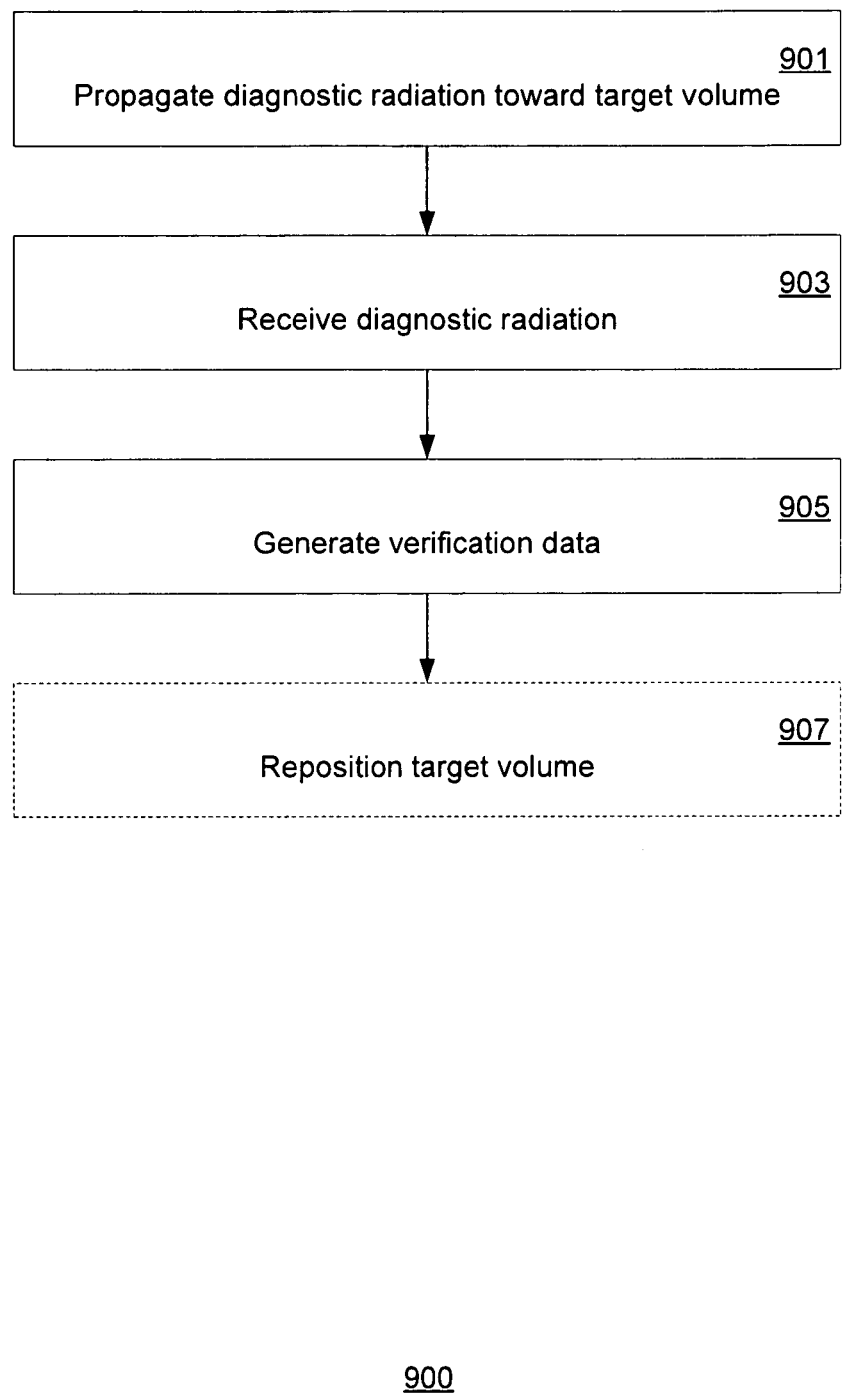
FIG. 9 is a flowchart of one embodiment of the method for applying radiation with a radiation therapy device in accordance with one embodiment.

FIG. 9 is a flowchart 900 of one embodiment of the method for applying radiation with a radiation therapy device in accordance with one embodiment. Steps 901-907 describe exemplary steps comprising the process depicted in flowchart 900 in accordance with the various embodiments herein described. In one embodiment, the flowchart 900 is implemented as computer-executable instructions stored in a computer-readable medium.

At step 901, diagnostic radiation from a diagnostic radiation source 211 coupled to a first robotic arm 207 is propagated towards a target volume. In one embodiment, the diagnostic radiation source 211 is a diagnostic X-ray source, and the diagnostic radiation is diagnostic X-ray radiation. In further embodiments, the diagnostic X-ray radiation is propagated as a cone beam. The target volume may be disposed in or about a subject positioned on patient couch 215. In one embodiment, the subject is positioned in a supine position and supported by patient couch 215. In some embodiments, the diagnostic radiation source 211 is positioned along a trajectory by movement of the coupled first robotic arm 207. Accordingly, diagnostic radiation may be propagated from the diagnostic radiation source 211 towards the target volume along the trajectory.

At step 903, an imager 213 coupled to a second robotic arm 209 receives the radiation propagated from the diagnostic radiation source 211 after the radiation has traveled through the target volume in step 901. According to some embodiments, steps 901 and 903 are performed simultaneously. In some embodiments, the diagnostic radiation source 211 is positioned along a trajectory by movement of the coupled first robotic arm 207. Accordingly, imager 213 may be positioned along a corresponding trajectory to receive propagated radiation from diagnostic radiation source 211. Positioning of imager 213 may be performed by movement of the coupled second robotic arm 209. In further embodiments, data from the received radiation is used to generate an image of the target volume. In still further embodiments, data from the received radiation is used to generate a volumetric image of the target volume. In further embodiments, the volumetric image of the target volume is displayed in computing device 217.

In one embodiment, the data received by the imager 213 from radiation propagated through the target volume and generated by diagnostic radiation source 211 is used to position the patient. Subsequently, radiation from a therapeutic radiation source 203 is propagated towards the target volume positioned on or about patient couch 215.

At step 905, the data received by the imager 213 from radiation propagated through the target volume and generated by diagnostic radiation source 211 may be used to verify the position of therapeutic radiation source 203. In one embodiment, the data received by the imager 213 is used to generate a plurality of three-dimensional volumetric images of the target volume. In further embodiments, the volumetric image of the target volume is displayed in computing device 217.

Finally, at optional step 907, verification data obtained in step 905 may be used to discover an improper or suboptimal position or alignment of the target volume. The target volume may be adjusted accordingly, so as to correct the position or alignment of the target volume with respect to the therapeutic radiation source 203.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation therapy device comprising:
   a gantry;
   a first radiation source mounted on the gantry;
   a plurality of robotic arms mounted to the gantry, the plurality of robotic arms including a first robotic arm and a second robotic arm;
   a second radiation source attached to the first robotic arm;
   an imager attached to the second robotic arm; and
   a computing device, communicatively coupled to the plurality of robotic arms, the computing device executing a flexible motion control system,
   wherein the radiation therapy device is configured to maneuver each of the plurality of robotic arms to acquire a plurality of three dimensional images taken along at least one acquisition trajectory of the plurality of acquisition trajectories programmed and customized for the patient via an interface of the flexible motion control system.

2. The device of claim 1, wherein control of each of the plurality of robotic arms is achieved through the flexible motion control system executing on the computing device.

3. The device of claim 2, wherein the flexible motion control system is operable to program a plurality of customizable acquisition trajectories for maneuvering each of the plurality of robotic arms independently of the other.

4. The device of claim 3, wherein a customizable acquisition trajectory comprises a user-programmed trajectory programmed in the flexible motion control system via a programming interface.

5. The device of claim 1, wherein an acquisition of a plurality of three dimensional images along a pre-programmed trajectory is achieved by maneuvering the plurality of robotic arms according to the pre-programmed trajectory.

6. The device of claim 1, wherein each of the plurality of robotic arms is retractable.

7. The device of claim 1, wherein each of the plurality of robotic arms is extendable.

8. The device of claim 1, wherein the radiation source is a diagnostic X-ray tube.

9. The device of claim 1, wherein the imager is a flat panel detector.

10. The device of claim 1, wherein the radiation source is a linear accelerator.

11. The system of claim 1, wherein the plurality of acquisition trajectories comprises a trajectory corresponding to a saddle cone beam computer tomography scan.

12. The system of claim 1, wherein the first radiation source is operable to propagate therapeutic radiation to a patient positioned via the plurality of three dimensional images taken along the plurality of acquisition trajectories customized for the patient.

13. A method for configuring a radiation therapy device, comprising:
    positioning a first robotic arm of a radiation therapy device along a plurality of acquisition trajectories around a target volume, the first robotic arm being coupled to a diagnostic X-ray source;
    positioning a second robotic arm of a radiation therapy device along the plurality of acquisition trajectories such that an imager coupled to the second robotic arm receives radiation from the diagnostic X-ray source; and
    acquiring a plurality of three dimensional volumetric images from the positioning of the first robotic arm and the positioning of the second robotic arm,
    wherein at least one acquisition trajectory of the plurality of acquisition trajectories is programmed and customized for the user through an interface of a motion control system communicatively coupled to the radiation therapy device.

14. The method of claim 13, further comprising:
    propagating diagnostic X-ray radiation from the diagnostic X-ray source toward the target volume; and
    receiving the diagnostic X-ray radiation in the imager after the diagnostic X-ray radiation passes through the target volume.

15. The method of claim 14, further comprising:
    generating verification data from the diagnostic X-ray radiation received in the imager; and
    re-positioning a target volume based on the verification data, wherein the diagnostic X-ray radiation comprises cone beam X-rays acquired via the plurality of acquisition trajectories customized for the target volume.

16. The method of claim 15, further comprising:
    propagating therapeutic radiation towards the target volume from a therapeutic radiation source after the target volume has been repositioned via the plurality of acquisition trajectories customized for the target.

17. The method of claim 13, wherein positioning a first robotic arm coupled to a diagnostic X-ray source comprises:
    accessing a pre-programmed customized trajectory; and
    automatically maneuvering the first robotic arm coupled to the diagnostic X-ray source according to the pre-programmed customized trajectory.

18. The method of claim 17, wherein positioning a second robotic arm coupled to an imager comprises:
    accessing a pre-programmed customized trajectory; and
    automatically adjusting the position of the second robotic arm coupled to an imager to align with maneuvering of the diagnostic X-ray source according to the pre-programmed customized trajectory.

19. A computer tomography system comprising:
    a gantry;
    a first extendable robotic arm mounted on the gantry, wherein the first extendable robotic arm is attached to an X-ray source that emits a cone-beam X-ray at a target;
    a second extendable robotic arm mounted on the gantry, wherein the second extendable robotic arm is attached to an imager that receives the cone-beam X-ray;
    a patient table for supporting the target; and
    a computing device, communicatively coupled to the first extendable robotic arm and the second extendable robotic arm, the computing device executing a motion control system,
    wherein each of the first extendable robotic arm and the second extendable robotic arm is operable to move along a plurality of acquisition trajectories communicated from the motion control system,
    wherein the computer tomography system is configured to acquire a plurality of three dimensional images taken along the plurality of acquisition trajectories,
    further wherein at least one acquisition trajectory of the plurality of acquisition trajectory is programmed and customized for the target via an interface of the motion control system.

20. The system of claim 19, wherein the trajectories communicated from the computing device comprise pre-programmed trajectories.

21. The system of claim 19, wherein the trajectories communicated from the computing device comprise trajectories customized for the target.

22. The system of claim 19, further comprising a therapeutic radiation source coupled to the gantry and disposed over the patient table, the therapeutic radiation source being operable to propagate therapeutic radiation to target positioned via the plurality of three dimensional images taken along the plurality of acquisition trajectories customized for the patient.

* * * * *